United States Patent [19]
Hieber et al.

[11] Patent Number: 5,877,326
[45] Date of Patent: Mar. 2, 1999

[54] AQUEOUS PHASE PROCESS FOR PREPARING N-SUBSTITUTED IMIDAZOLES

[75] Inventors: Gisela Hieber, Heidelberg; Klaus Ebel, Lampertheim; Jürgen Schröder, Ludwigshafen; Toni Dockner, Meckenheim; Carsten Gröning, Mannheim; Bernd Ruge, Böhl-Iggelheim, all of Germany

[73] Assignee: BASF Aktiengesellschaft, Ludwigshafen, Germany

[21] Appl. No.: 914,187

[22] Filed: Aug. 19, 1997

[30] Foreign Application Priority Data

Aug. 19, 1996 [DE] Germany ............... 196 333 90.3

[51] Int. Cl.⁶ ............. C07D 233/54; C07D 233/56; C07D 233/58
[52] U.S. Cl. .................. 548/335.1; 548/343.5; 548/345.1; 548/346.1
[58] Field of Search ................ 548/335.1, 346.1

[56] References Cited

U.S. PATENT DOCUMENTS

| 3,177,223 | 4/1965 | Erner ........................... 548/335.1 |
| 3,652,581 | 3/1972 | Spaenig et al. ............. 548/335.1 X |
| 3,843,676 | 10/1974 | Spaenig et al. ............ 548/335.1 |
| 5,179,210 | 1/1993 | Ebel .............................. 548/335.1 |
| 5,283,341 | 2/1994 | Tanaka et al. ............... 548/262.2 |

FOREIGN PATENT DOCUMENTS

| 1 670 293 | 12/1967 | Germany . |
| 21 06 877 | 2/1971 | Germany . |
| 22 33 908 | 7/1972 | Germany . |
| 1659408 | 6/1991 | U.S.S.R. ...................... 548/335.1 |
| 0626475 | 7/1949 | United Kingdom ......... 548/335.1 |
| 1 243 078 | 8/1971 | United Kingdom . |
| 1 426 834 | 3/1976 | United Kingdom . |

OTHER PUBLICATIONS

Tanaka et al., *Chemistry Letters*, No. 4, Apr. 1992, pp. 575–578.
*J. Chem. Soc. Chem. Commun.*, vol. 9, 1995, p. 9.
Houben–Weyl, *Methoden der organischen Chemie*, E 8c, Hetarene III/Teil 3, pp. 4–214.

*Primary Examiner*—Floyd D. Higel
*Attorney, Agent, or Firm*—Keil & Weinkauf

[57] ABSTRACT

A process for preparing substituted imidazoles of the formula I

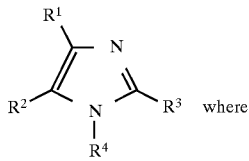

$R^1$, $R^2$ and $R^3$ are identical or different and are each hydrogen, halogen, $NO_2$, CN or a $C_1$–$C_{20}$-hydrocarbon radical which is unsubstituted or substituted by one or more halogens or $R^1$ and $R^2$ together are members of a 3- to 20-membered hydrocarbon ring which is unsubstituted or substituted by one or more halogens and/or $C_1$–$C_8$-alkyl groups and which may contain 1, 2 or 3 heteroatoms from the group consisting of nitrogen, oxygen and sulfur, and $R^4$ is a $C_1$–$C_{20}$-hydrocarbon radical which is unsubstituted or substituted by one or more halogens, comprises using an aqueous phase of the imidazoles of the formula II

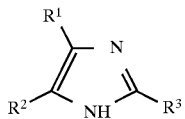

where $R^1$, $R^2$ and $R^3$ are as defined above with compounds of the formula III

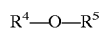

where $R^4$ is as defined above and $R^5$ is hydrogen or $R^4$, it being possible in the latter case for the two $R^4$ substituents to be identical or different, and reacting it at from 200° to 550° C. in the presence of a catalyst comprising oxides and/or phosphates of one or more metals of the 2nd, 3rd and 4th main group and the 4th subgroup of the Periodic Table in the presence or absence of phosphoric acid and/or phosphoric esters.

22 Claims, No Drawings

AQUEOUS PHASE PROCESS FOR PREPARING N-SUBSTITUTED IMIDAZOLES

The present invention relates to a process for preparing substituted imidazoles of the general formula I

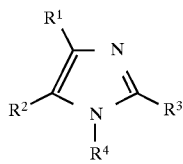

where

R$^1$, R$^2$ and R$^3$ are identical or different and are each hydrogen, halogen, NO$_2$, CN or a C$_1$–C$_{20}$-hydrocarbon radical which is unsubstituted or substituted by one or more halogens or R$^1$ and R$^2$ together are members of a 3- to 20-membered hydrocarbon ring which is unsubstituted or substituted by one or more halogens and/or C$_1$–C$_8$-alkyl groups and which may contain 1, 2 or 3 heteroatoms from the group consisting of nitrogen, oxygen and sulfur, and R$^4$ is a C$_1$–C$_{20}$-hydrocarbon radical which is unsubstituted or substituted by one or more halogens, which comprises using an aqueous phase of the imidazoles of the formula II

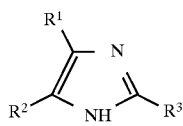

where R$^1$, R$^2$ and R$^3$ are each as defined above, with compounds of the formula III

where

R$^4$ is as defined above and

R$^5$ is hydrogen or R$^4$, it being possible in the latter case for the two R$^4$ substituents to be identical or different, and reacting it at from 200° to 550° C. in the presence of a catalyst comprising oxides and/or phosphates of one or more metals of the 2nd, 3rd and 4th main group and the 4th subgroup of the Periodic Table in the presence or absence of phosphoric acid and/or phosphoric esters.

DE-A-16 70 239, DE-A-21 06 877, DE-B-22 33 908 and Yoshio Ono et al., J. Chem. Soc., Chem. Commun. 9, (1995) disclose processes for preparing substituted imidazoles by reacting imidazoles in alcohol and/or ether phases in the presence of a catalyst to give the desired substituted imidazole. All these process have the disadvantage that no aqueous imidazole phases are used for preparing the desired imidazoles. According to Houben-Weyl, *Methoden der organischen Chemie,* Georg Thieme-Verlag, Stuttgart-New York, E 8c, Hetarene III/Part 3, 4 ff, as-synthesized imidazoles are normally obtained in an aqueous phase.

Further reactions with alcohols or ethers as per the processes known from the prior art would require a change of solvent. In large-scale industrial processes, in particular, such a change of solvent is associated with considerable technical complications and energy expenditure, and therefore with considerable costs.

A pumpable solution suitable for the reaction can only be obtained by dissolving the imidazoles in alcohols or ethers with which they are to be reacted. To employ the imidazoles directly without solvent, it would be necessary to use the melts of the imidazoles. This is disadvantageous since the imidazoles, as a rule, have melting points between 100° and 200° C., 2-methylimidazole, for example, having a melting point of 137° C. Using temperatures in the range from 100° to 200° C. is associated with considerable technical complications and leads to decomposition products of the imidazoles used interfering with the reaction.

The aqueous imidazole phase obtained in the synthesis of imidazoles, however, possesses excellent pumpability, an imidazole phase consisting of 70% by weight of 2-methylimidazole and 30% by weight of water, for example, having a melting point of about 70° C. The processes known from the prior art have the disadvantage that the excellently pumpable aqueous imidazole phases cannot be used. It is furthermore generally known that in condensation reactions, in particular in condensation reactions where the condensation product is water, the presence of water is a disadvantage because, according to the law of mass action, the reaction equilibrium is shifted to the reactant side.

It is an object of the present invention to provide a process which overcomes the aforementioned disadvantages and which, in particular, allows the direct use of an aqueous imidazole phase obtained in the synthesis of imidazoles for preparing the substituted imidazoles according to the invention.

We have found that this object is achieved by a process as defined above.

For an aqueous 2-methylimidazole solution and methanol, the reaction can be represented by the following formula:

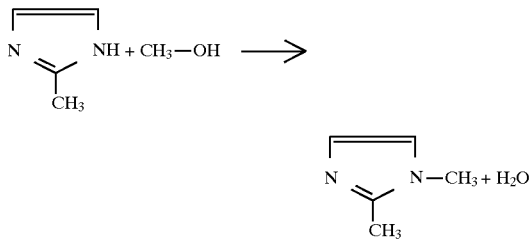

In comparison to the prior art processes, the process according to the invention makes available a large number of N-substituted imidazoles by a simpler route and in identical or better yields and purities.

For the purposes of the invention, it can be advantageous for the C$_1$–C$_{20}$-hydrocarbon to be, for example, a C$_3$–C$_{12}$-hydrocarbon ring, C$_6$–C$_{18}$-aryl and C$_7$–C$_{20}$-aralkyl. In addition, preference is given to C$_1$–C$_{10}$-hydrocarbons and particular preference is given to C$_1$–C$_6$-hydrocarbons.

Hydrocarbon radicals according to the invention are preferably aliphatic radicals, such as C$_1$–C$_{20}$-alkyl, preferably C$_1$–C$_{10}$-alkyl, particularly preferably C$_1$–C$_5$-alkyl. C$_1$–C$_5$-alkyl radicals include methyl, ethyl, n-propyl, isopropyl, n-butyl, isobutyl, tert-butyl, n-pentyl, 2-methylbutyl and 3-methylbutyl, of which methyl, ethyl, n-propyl and isopropyl are preferred and methyl and ethyl are particularly preferred.

Further hydrocarbon radicals preferred according to the invention are for example aliphatic radicals, such as C$_2$–C$_{20}$-alkenyl, preferably C$_2$–C$_{10}$-alkenyl and particularly preferably C$_2$–C$_5$-alkenyl. C$_2$–C$_5$-alkenyl radicals include for example ethenyl, propenyl, 1-butenyl, 2-butenyl, 3-butenyl, 1,3-butadienyl, tert-butenyl, 1-pentenyl, 2-pentenyl, 3-pentenyl, 4-pentenyl and isoprenyl. Aliphatic radicals according to the invention are for example alkynyl radicals such as C$_3$–C$_{20}$-alkynyl, preferably C$_3$–C$_{10}$-alkynyl and particularly preferably $C_3$–$C_5$-alkynyl. They include for example ethynyl, propynyl, 1-butynyl, 2-butynyl, 3-butynyl, 1-pentynyl, 2-pentynyl, 3-pentynyl and 4-pentynyl.

Further aliphatics preferred according to the invention are hydrocarbon rings, such as $C_3$–$C_{12}$-cycloalkyl, preferably $C_3$–$C_8$-cycloalkyl and particularly preferably $C_3$–$C_6$-cycloalkyl. $C_3$–$C_6$-cycloalkyl radicals according to the invention are cyclopropyl, cyclobutyl, cyclopentyl and cyclohexyl, cyclobutyl, cyclopentyl and cyclohexyl being preferred and cyclopentyl and cyclohexyl being particularly preferred.

The hydrocarbon rings according to the invention preferably contain one or more double bonds and/or triple bonds, possible ring radicals having one double bond being, for example, cyclopropenyl, cyclobutenyl, cyclopentenyl, cyclohexenyl and cycloheptenyl and possible cyclic radicals having two double bonds being cyclopentadienyl and 2,4-cyclohexadienyl.

Aryl radicals according to the invention are, for example, phenyl, naphthyl and anthracenyl which are unsubstituted or substituted by one or more $C_1$–$C_8$-alkyl radicals and/or halogens. Alkylaryl radicals are, for example, toluyl or xylyl which are unsubstituted or substituted by one or more halogens. Preferred halogenated aryl radicals according to the invention are, for example, aromatics which are substituted one or more times by halogen, such as fluorine, chlorine, bromine or iodine, preferably fluorine, chlorine or bromine, particularly preferably chlorine, for example 2-, 3- and 4-chlorophenyl, 2,4-dichlorophenyl, 2,6-dichlorophenyl and 2,4,6-trichlorophenyl.

Preferred aralkyl radicals according to the invention, which are optionally halogen-substituted anywhere and/or substituted by $C_1$–$C_6$-alkyl in the aromatic moiety, are benzyl, 1-phenylethyl, 2-phenylethyl, 1-phenylpropyl, 2-phenylpropyl, 1-phenylbutyl, 2-phenylbutyl, 3-phenylbutyl and 1-phenylpentyl.

$R^1$, $R^2$ and $R^3$ may furthermore, independently of one another, be halogen, such as fluorine, chlorine, bromine or iodine, preferably fluorine, chlorine or bromine, particularly preferably chlorine.

In addition, $R^1$ and $R^2$ together may be members of a 3- to 20-membered, preferably 3- to 10-membered, particularly preferably 3- to 6-membered, hydrocarbon ring which is unsubstituted or substituted by one or more halogens and/or $C_1$–$C_8$-alkyl groups and which may contain 1, 2 or 3 heteroatoms from the group consisting of nitrogen, oxygen and sulfur. The ring heteroatoms are preferably bonded in such a way that they are not attached to a hydrogen, as for example in the case of purine.

Preference according to the invention is given to mono- or polyunsaturated hydrocarbon rings not having any heteroatoms. Preferred hydrocarbon rings formed by $R^1$ and $R^2$ and having one or more double bonds and/or triple bonds are for example rings having one double bond, such as cyclopropenyl, cyclobutenyl, cyclopentenyl, cyclohexenyl and cycloheptenyl rings. Preferred hydrocarbon rings formed by $R^1$ and $R^2$ having two double bonds are cyclopentadienyl and 2,4-cyclohexadienyl rings. $R^1$ and $R^2$ may also be members of a hydrocarbon ring having conjugated double bonds, the number of the conjugated double bonds preferably being from 2 to 7 and the rings being present, according to the rule of Hückel, either as an aromatic or conjugated π-electron system. An imidazole having such a ring is for example benzimidazole.

In addition to imidazole, the following substituted imidazoles may preferably be used as starting material II:

2-methyl-, 2-ethyl-, 2-n-propyl-, 2-isopropyl-, 2-n-butyl-, 2-isobutyl-, 2-tert-butyl- and 2-phenyl-imidazole and the corresponding 4 or 5-substituted imidazoles;

2-methyl-4-ethyl-, 2,4-dimethyl-, 2,4-diphenyl- and the corresponding 2,5- and 4,5-substituted imidazoles;

2-phenyl-4methyl-5-ethyl-, 4methyl-5-phenyl-, 5-methyl-4-phenyl-, 2,4,5-trimethylimidazole and 4,5-dimethylimidazole.

According to the invention, the starting materials II as aqueous phase are preferably employed in a ratio of from 0.1 to 99.9, preferably from 50 to 99 and particularly preferably from 60 to 90% by weight of starting material II to from 99.9 to 0.1, preferably from 50 to 1 and particularly preferably from 40 to 10% by weight of water, the sum of the % by weight of starting material II and water in each case being 100. The starting materials II are particularly preferably employed in aqueous phases as obtained in the synthesis of the starting material II to be employed. The aqueous phases according to the invention may be solutions, suspensions, emulsions, slurries, etc., suspensions and slurries being preferred and suspensions being particularly preferred. Furthermore, agents increasing the solubility and/or pumpability of the starting material II, for example soaps and surface-active agents, may be present in the aqueous phases according to the invention.

Preferred aliphatic radicals $R^4$ according to the invention are $C_1$–$C_{20}$-alkyl, preferably $C_1$–$C_{10}$-alkyl and particularly preferably $C_1$–$C_5$-alkyl. $C_1$–$C_5$-alkyl radicals include methyl, ethyl, n-propyl, isopropyl, n-butyl, isobutyl, tert-butyl, n-pentyl, 2-methylbutyl and 3-methylbutyl, methyl, ethyl, n-propyl and isopropyl being preferred and methyl and ethyl being particularly preferred.

Further preferred aliphatic radicals $R^4$ according to the invention are $C_2$–$C_{20}$-alkenyl, preferably $C_2$–$C_{10}$-alkenyl and particularly preferably $C_2$–$C_5$-alkenyl. $C_2$–$C_5$-alkenyl radicals include, for example, ethenyl, propenyl, 1-butenyl, 2-butenyl, 3-butenyl, 1,3-butadienyl, tert-butenyl, 1-pentenyl, 2-pentenyl, 3-pentenyl, 4-pentenyl and isoprenyl. $R^4$ is preferably 2-buten-1-yl, 2-penten-1-yl, 2,2-dimethylpenten-1-yl.

Other preferred aliphatic radicals $R^4$ according to the invention are $C_3$–$C_{20}$-alkynyl, preferably $C_3$–$C_{10}$-alkynyl and particularly preferably $C_3$–$C_5$-alkynyl. These include for example propynyl, 1-butynyl, 2-butynyl, 3-butynyl, 1-pentynyl, 2-pentynyl, 3-pentynyl and 4-pentynyl. Particularly suitable alkynyl radicals $R^4$ are propynyl, 1,1-dimethylpropynyl, 1-methylpropynyl and 1-butynyl.

Further preferred aliphatic radicals $R^4$ according to the invention are $C_3$–$C_{12}$-cycloalkyl, preferably $C_3$–$C_8$-cycloalkyl and particularly preferably $C_3$–$C_6$-cycloalkyl. $C_3$–$C_6$-cycloalkyl radicals $R^4$ according to the invention are cyclopropyl, cyclobutyl, cyclopentyl and cyclohexyl, cyclobutyl, cyclopentyl and cyclohexyl being preferred and cyclopentyl and cyclohexyl being particularly preferred. Aliphatic radicals $R^4$ according to the invention are likewise hydrocarbon rings carrying one or more double bonds, radicals having one double bond including, for example, cyclopropenyl, cyclobutenyl, cyclopentenyl, cyclohexenyl and cycloheptenyl and cyclic radicals having two double bonds including cyclopentadienyl and 2,4cyclohexadienyl.

Further preferred aliphatic radicals $R^4$ according to the invention are cycloalkylalkyl radicals, for example cyclopropylmethyl and cyclohexylmethyl.

Preferred aralkyl radicals $R^4$ according to the invention are, for example, benzyl, phenylethyl, phenylpropyl and phenylbutyl.

The radical $R^5$ according to the invention is hydrogen or has, independently of $R^4$, the same meanings, $R^5$ particularly preferably being hydrogen.

In the starting material III, $R^5$ is preferably a radical having a molecular weight identical to or lower than $R^4$. In particularly preferred starting materials III, the radicals $R^4$ and $R^5$ agree with respect to the electrophilicity of the carbons attached to the oxygen. Furthermore, particular preference is given to startng materials where $R^5$ is hydrogen.

Preference according to the invention is further given to substituents $R^4$ and $R^5$ which differ from each other as much as possible with respect to their molecular weight and their structure and in electrophilicity. Particular preference according to the invention is given to radicals $R^4$ and $R^5$ which differ from each other with respect to the electrophilicity of the carbon attached to the oxygen as well as in their molecular weight. In addition to what has been mentioned before, it may be advantageous for the process according to the invention if $R^4$ and $R^5$ have matching molecular weights but differ from each other with respect to the electronegativity of the carbons bonded to the oxygen.

The following alcohols or ethers can, for example, be used as starting materials III: methanol, ethanol, n-propanol, isopropanol, n-butanol, sec-butanol, tert-butanol, pentanol, hexanol, heptanol, octanol, nonanol, decanol, undecanol, dodecanol and the dialkyl ethers corresponding to the aforementioned alcohols: methyl ethyl ether, methyl-n-propyl ether, methyl isopropyl ether, methyl n-butyl ether, methyl sec-butyl ether, methyl tert-butyl ether, methyl pentyl ether, methyl hexyl ether, methyl heptyl ether, methyl octyl ether, methyl nonyl ether, methyl decyl ether, methyl-undecyl ether, methyl dodecyl ether and the corresponding ethyl alkyl ethers, benzyl propyl ether, etc.

The process according to the invention is carried out in the presence of catalysts comprising oxides and/or phosphates of one or more metals of the 2nd, 3rd and 4th main group and the 4th subgroup of the Periodic Table, in the presence or absence of phosphoric acid and/or phosphoric esters. Preference is given to the lower homologs of metals of the 2nd, 3rd and 4th main group and the 4th subgroup of the Periodic Table, in particular calcium aluminum, silicon, titanium, but also zirconium and thorium. The oxides and/or phosphates of the aforementioned metals may be added to the reaction singly or in any mixture with each other.

Preference is given to using phosphoric acid and/or one or more phosphoric esters as auxiliary catalysts in addition to the oxides and/or phosphates of the aforementioned metals.

In the esters, the phosphoric acid can be esterified once, preferably two times or more preferably three times; mixtures of these phosphoric esters may likewise be preferred. Suitable are for example pyro-, meta- and in particular orthophosphoric acid; cycloaliphatic, araliphatic, aromatic and in particular aliphatic esters of phosphoric acid. Preference is given in particular to esters having 1 to 12 carbons, such as triethyl, tri-n-butyl, trimethyl, O,O-diethyl-O-phenyl, O-ethyl-O-O-diphenyl-, tricyclohexyl, tribenzyl, O,O-dimethyl-O-ethyl, tris-2-ethylhexyl, tris-β-chloroethyl, tris-β-butoxyethyl, tris-β-methoxyethyl, di-(2ethylhexyl), dioctyl, octadecyl, tricresyl, O,O-diphenyl-O-cresyl, trixylenyl, tris-(p-tert-butylphenyl), O,O-diphenyl-O-bisphenyl and O,O-diphenyl-O-methyl esters of phosphoric acid.

Prior to use, the structure or the surface of the catalysts can be modified by physical and/or chemical treatment, for example by roasting, treatment with water vapor, impregnating with acids, for example phosphoric acid or hydrochloric acid, or for example by the nitrates, formates or oxalates of the aforementioned metals. The catalyst can be applied to a carrier material for example by impregnation or precipitation and may be converted into its final oxide form by thermal treatment or decomposition. Suitable carrier materials are, for example, various silicon dioxides, in particular silicic acid compounds, such as silicates, for example sodium silicate and calcium silicate, bleaching earths, argilaceous earths, kaolin, zeolites, pumice, bentonites, silica, silica gel, diatomaceous earth, etc. The carrier materials may further comprise compounds of other elements, for example sodium, which do not influence the reaction significantly. It is furthermore advantageous to employ a fixed-bed catalyst or a fluidized-bed catalyst for the reaction.

Preferred catalysts for the purposes of the invention comprise from 40 to 99% by weight of $SiO_2$ and from 1 to 60% by weight of $H_3PO_4$, particularly preferably from 70 to 95% by weight of $SiO_2$ and from 5 to 30% by weight of $H_3PO_4$. Another catalyst which is preferred for the purposes of the invention comprises from 30 to 99% by weight of $Al_2O_3$ and from 1 to 70% by weight of $SiO_2$, particularly preferably from 70 to 90% by weight of $Al_2O_3$ and from 10 to 30% by weight of $SiO_2$. The sum of all components of the catalysts according to the invention is in each case 100%.

It is also possible, in addition to the preferred practice of the process according to the invention in a fixed-bed reactor using a fixed-bed catalyst, to carry out the process according to the invention in other reactor types using other catalyst preparations, for example in a fluidized-bed reactor using a catalyst appropriately prepared for this purpose.

The process according to the invention may preferably be carried out in the following way: in a tubular, fluidized-bed or fixed-bed reactor, in the presence or absence of an inert gas atmosphere, for example of nitrogen or argon, a mixture of the starting materials II and III is passed over the catalyst which has been heated to reaction temperature. The reaction product can, if desired, be worked up using known procedures, for example chromatography or fractional distillation. The process according to the invention is preferably carried out as a gas phase reaction.

In a particularly preferred embodiment of the process according to the invention, the pumpable aqueous phases of the imidazoles to be substituted are used as starting materials II. In a particularly preferred embodiment of the process according to the invention, 2-methylimidazole is employed as a pumpable aqueous phase as starting material II. Particularly preferred starting materials II are the aqueous imidazole phases originating directly from the imidazole synthesis. In the aforementioned embodiments of the process according to the invention, it can be preferable to heat the aqueous imidazole phase so that its pumpability is optimal. In a further particularly preferred embodiment of the process according to the invention, an aqueous phase liquefied in the temperature range from 60° to 80° C. and comprising 70% by weight of 2-methylimidazole and 30% by weight of water is employed.

The reaction is carried out at from 200° to 550° C., preferably at from 250° to 450° C. particularly preferably at from 280° to 420° C.

The compounds prepared by the process according to the invention are useful in particular as precursors and intermediates and as catalysts in the preparation of dyes, textile auxiliaries, drugs, plastics and crop protection agents.

The Examples which follow illustrate the invention. Parts are by weight.

EXAMPLES

Example 1

In a continuously operated fixed-bed reactor, a mixture of 10.6 parts of 2-methylimidazole, 5 parts of water and 12.4 parts of methanol is passed per hour over the fixed-bed catalyst (80% by weight of $SiO_2$, 20% by weight of $H_3PO_4$) at 330° C. At certain intervals, a sample of the crude effluent is analyzed by gas chromatography. The conversion is 100%, the yield is 96%.

Example 2

In a continuously operated fixed-bed reactor, a mixture of 10.6 parts of 2-methylimidazole, 5 parts of water and 25.6 parts of methanol is passed per hour over the fixed-bed catalyst (80% by weight of $Al_2O_3$, 20% by weight of $SiO_2$) at 350° C. At certain intervals, a sample of the crude effluent is analyzed by gas chromatography. Determined similarly to Example 1, the conversion is 98% and the yield is 94%.

We claim:

1. A process for preparing substituted imidazoles of the formula I

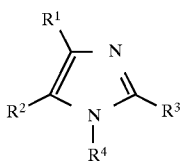

where $R^1$, $R^2$ and $R^3$ are identical or different and are each hydrogen, halogen, $NO_2$, CN or a $C_1$–$C_{20}$-hydrocarbon radical which is unsubstituted or substituted by one or more halogens or $R^1$ and $R^2$ together are members of a 3- to 20-membered hydrocarbon ring which is unnubstituted or substituted by one or more halogens and/or $C_1$–$C_8$-alkyl groups, which hydrocarbon ring does or does not contain 1, 2 or 3 heteroatoms from the group consisting of nitrogen, oxygen and sulfur, and $R^4$ is a $C_1$–$C_{20}$-hydrocarbon radical which is unsubstituted or substituted by one or more halogens, by reacting as starting material an aqueous phase of the imidazoles of the formula II

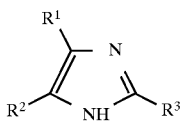

where $R^1$, $R^2$ and $R^3$ are as defined above with compounds of the formula III

where $R^4$ is as defined above and $R^5$ is hydrogen or $R^4$, it being possible in the latter case for the two $R^4$ substituents to be identical or different, and reacting it at from 200° to 550° C. in the presence of a catalyst comprising oxides or phosphates of one or more metals of the 2nd, 3rd and 4th main group and the 4th subgroup of the Periodic Table in the presence or absence of phosphoric acid and phosphoric esters.

2. The process of claim 1 wherein the $C_1$–$C_{20}$-hydrocarbon is $C_1$–$C_{20}$-alkyl, $C_2$–$C_{20}$-alkenyl, $C_3$–$C_{20}$-alkinyl, a $C_3$–$C_{12}$-hydrocarbon ring, $C_6$–$C_{18}$-aryl or $C_2$–$C_{20}$-aralkyl.

3. The process of claim 1 wherein the reaction is carried out at from 250° to 450° C. in the presence or absence of phosphoric acid using a catalyst comprising silicon oxides, aluminum oxides or muxtures thereof.

4. The process of claim 1 wherein the reaction is carried out in the presence of a catalyst comprising from 40 to 99% by weight of $SiO_2$ and from 1 to 60% by weight of $H_3PO_4$.

5. The process of in claim 1 wherein the reaction is carried out in the presence of a catalyst comprising from 30 to 99% by weight of $Al_2O_3$ and from 1 to 70% by weight of $SiO_2$.

6. The process of claim 1 wherein the reaction is carried out using an aqueous imidazole phase having a ratio of from 0.1 to 99.9% by weight of imidazole of the formula II to from 0.1 to 99.9% by weight of water.

7. The process of claim 1 wherein the reaction is carried out using a fixed-bed catalyst.

8. The process of claim 1 wherein the reaction is carried out in the gas phase.

9. The process of claim 1 wherein the reaction is carried out in a continuous manner.

10. The process of claim 1 wherein the starting material is the aqueous product mixture from the preparation of imidazoles of the formula II.

11. A process for preparing substituted imidazoles of the formula I

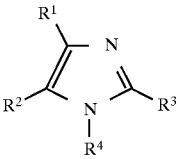

where $R^1$, $R^2$ and $R^3$ are identical or different and are each hydrogen, halogen, $NO_2$, CN or a $C_1$–$C_{20}$-hydrocarbon radical which is unsubstituted or substituted by one or more halogens or $R^1$ and $R^2$ together are members of a 3- to 20-membered hydrocarbon ring is which is unsubstituted or substituted by one or more halogens and/or $C_1$–$C_8$-alkyl groups and which does or does not contain 1, 2 or 3 heteroatoms from the group consisting of nitrogen, oxygen and sulfur, and $R^4$ is a $C_1$–$C_{20}$-hydrocarbon radical which is unsubstituted or substituted by one or more halogens, by reacting as starting material an aqueous phase of the imidazoles of the formula II

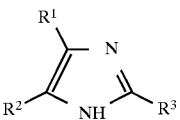

where $R^1$, $R^2$ and $R^3$ are as defined above with compounds of the formula III

where $R^4$ is as defined above and $R^5$ is hydrogen or $R^4$, it being possible in the latter case for the two $R^4$ substituents to be identical or different, and reacting it at from 200° to 550° C. in the presence of a catalyst comprising oxides, phosphates, or mixtures thereof of one or more metals of the 2nd, 3rd and 4th main group and the 4th subgroup of the Periodic Table in the presence or absence of phosphoric acid and/or phosphoric esters, wherein the $C_1$–$C_{20}$-hydrocarbon is $C_1$–$C_{20}$-alkyl, $C_2$–$C_{20}$- alkenyl, $C_3$–$C_{20}$-alkinyl, a $C_3$–$C_{12}$-hydrocarbon ring, $C_6$–$C_{18}$-aryl or $C_2$–$C_{20}$-aralkyl.

12. The process of claim 11 wherein the reaction is carried out at from 250° to 450° C. in the presence or absence of phosphoric acid using a catalyst comprising silicon oxides, aluminum oxides and mixtures thereof.

13. The process of claim 11 wherein the reaction is carried out in the presence of a catalyst comprising from 40 to 99% by weight of $SiO_2$ and from 1 to 60% by weight of $H_3PO_4$.

14. The process of claim 11 wherein the reaction is carried out in the presence of a catalyst comprising from 30 to 99% by weight of $Al_2O_3$ and from 1 to 70% by weight of $SiO_2$.

15. The process of claim 11 wherein the reaction is carried out using an aqueous imidazole phase having a ratio of from 0.1 to 99.9% by weight of imidazole of the formula II to from 0.1 to 99.9% by weight of water.

16. A process of claim 11 wherein the reaction is carried out using a fixed-bed catalyst.

17. A process of claim 11 wherein the reaction is carried out in the gas phase.

18. A process of claim 11 wherein the starting material used is the aqueous product mixture from the preparation of imidazoles of the formula II.

19. A process for preparing substituted imidazoles of the formula I

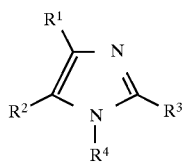

where
$R^1$, $R^2$ and $R^3$ are identical or different and are each hydrogen, halogen, $NO_2$, CN or a $C_1$–$C_{20}$-hydrocarbon radical which is unsubstituted or substituted by one or more halogens or $R^1$ and $R^2$ together are members of a 3- to 20-membered hydrocarbon ring which is unsubstituted or substituted by one or more halogens and/or $C_1$–$C_8$-alkyl groups and which does or does not contain 1, 2 or 3 heteroatoms from the group consisting of nitrogen, oxygen and sulfur, and $R^4$ is a $C_1$–$C_{20}$-hydrocarbon radical which is unsubstituted or substituted by one or more halogens, by reacting
as starting material an aqueous phase of the imidazoles of the formula II

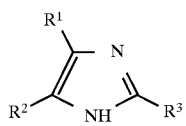

where $R^1$, $R^2$ and $R^3$ are as defined above with compounds of the formula III

 III where
$R^4$ is as defined above and
$R^5$ is hydrogen or $R^4$, it being possible in the latter case for the two $R^4$ substituents to be identical or different, and
reacting it at from 200° to 550° C. in the presence of a catalyst comprising oxides, phosphates, or mixtures thereof of one or more metals of the 2nd, 3rd and 4th main group and the 4th subgroup of the Periodic Table in the presence or absence of phosphoric acid or phosphoric esters, wherein the $C_1$–$C_{20}$-hydrocarbon is $C_1$–$C_{20}$-alkyl, $C_2$–$C_{20}$-alkenyl, $C_3$–$C_{20}$-alkinyl, a $C_3$–$C_{12}$-hydrocarbon ring, $C_6$–$C_{18}$-aryl or $C_2$–$C_{20}$-aralkyl, wherein the reaction is carried out in the presence of a catalyst comprising from 40 to 99% by weight of $SiO_2$ and from 1 to 60% by weight of $H_3PO_4$.

20. A process for preparing substituted imidazoles of the formula I

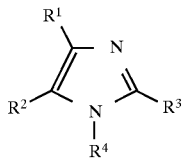

where
$R^1$, $R^2$ and $R^3$ are identical or different and are each hydrogen, halogen, $NO_2$, CN or a $C_1$–$C_{20}$-hydrocarbon radical which is unsubstituted or substituted by one or more halogens or $R^1$ and $R^2$ together are members of a 3- to 20-membered hydrocarbon ring which is unsubstituted or substituted by one or more halogens and/or $C_1$–$C_8$-alkyl groups and which may contain 1, 2 or 3 heteroatoms from the group consisting of nitrogen, oxygen and sulfur, and $R^4$ is a $C_1$–$C_{20}$-hydrocarbon radical which is unsubstituted or substituted by one or more halogens, by reacting
as starting material an aqueous phase of the imidazoles of the formula II

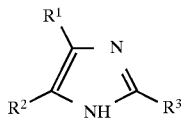

where $R^1$, $R^2$ and $R^3$ are as defined above with compounds of the formula II

 III where
$R^4$ is as defined above and
$R^5$ is hydrogen or $R^4$, it being possible in the latter case for the two $R^4$ substituents to be identical or different, and
reacting it at from 200° to 550° C. in the presence of a catalyst comprising oxides and/or phosphates of one or more metals of the 2nd, 3rd and 4th main group and the 4th subgroup of the Periodic Table in the presence or absence of phosphoric acid or phosphoric esters, wherein the $C_1$–$C_{20}$-hydrocarbon is $C_1$–$C_{20}$-alkyl, $C_2$–$C_{20}$-alkenyl, $C_3$–$C_{20}$-alkinyl, a $C_3$–$C_{12}$-hydrocarbon ring, $C_6$–$C_{18}$-aryl or $C_2$–$C_{20}$-aralkyl, wherein the reaction is carried out in the presence of a catalyst comprising from 30 to 99% by weight of $Al_2O_3$ and from 1 to 70% by weight of $SiO_2$.

21. The process of claim 10, wherein the imidazole of the formula II is 2-methylimidazole.

22. The process of claim 18, wherein the imidazole of the formula II is 2-methylimidazole.

* * * * *

UNITED STATES PATENT AND TRADEMARK OFFICE
CERTIFICATE OF CORRECTION

PATENT NO. : 5,877,326

DATED : March 2, 1999

INVENTOR(S) : HIEBER et al.

It is certified that error appears in the above-indentified patent and that said Letters Patent is hereby corrected as shown below:

Col. 8, claim 11, line 37, "ring is which is" should be --ring which is--.

Col. 10, claim 20, line 41, "formula II" should be --formula III--.

Signed and Sealed this

Fifth Day of October, 1999

Attest:

Q. TODD DICKINSON

Attesting Officer

Acting Commissioner of Patents and Trademarks